(12) United States Patent
Yamada

(10) Patent No.: US 11,693,226 B2
(45) Date of Patent: Jul. 4, 2023

(54) ENDOSCOPE

(71) Applicant: FUJIFILM Corporation, Tokyo (JP)

(72) Inventor: Hideyuki Yamada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 327 days.

(21) Appl. No.: 15/706,768

(22) Filed: Sep. 18, 2017

(65) Prior Publication Data

US 2018/0000316 A1 Jan. 4, 2018

Related U.S. Application Data

(63) Continuation of application No. PCT/JP2016/058008, filed on Mar. 14, 2016.

(30) Foreign Application Priority Data

Mar. 31, 2015 (JP) .................................. 2015-071819

(51) Int. Cl.
*G02B 23/24* (2006.01)
*A61B 1/05* (2006.01)
(Continued)

(52) U.S. Cl.
CPC ........ *G02B 23/2423* (2013.01); *A61B 1/0011* (2013.01); *A61B 1/00096* (2013.01);
(Continued)

(58) Field of Classification Search
CPC .............. A61B 1/0008; A61B 1/00096; A61B 1/00163; A61B 1/00165; A61B 1/05;
(Continued)

(56) References Cited

U.S. PATENT DOCUMENTS 4,895,138 A * 1/1990 Yabe ........................ A61B 1/05
348/E5.027
5,191,879 A * 3/1993 Krauter .............. A61B 1/00188
359/823
(Continued)

FOREIGN PATENT DOCUMENTS

AU 6943191 7/1991
JP H03-207334 9/1991
(Continued)

OTHER PUBLICATIONS

"Office Action of Japan Counterpart Application," dated Aug. 1, 2018, with English translation thereof, pp. 1-6.
(Continued)

*Primary Examiner* — Ryan N Henderson
*Assistant Examiner* — Pamela F Wu
(74) *Attorney, Agent, or Firm* — JCIPRNET

(57) ABSTRACT

Provided is an endoscope that can connect proximal ends of the first signal lines and a signal relay part together without securing an extra length for the first signal lines. An airtight casing is disposed inside an outer tube of an insertion part, an imaging device and first signal lines are accommodated inside the airtight casing, a distal end of the airtight casing is airtightly sealed by a cover glass, and a proximal end of the airtight casing is airtightly sealed by a partition wall part. The airtight casing is constituted of a first tubular body and a second tubular body, and the second tubular body is disposed in a nested shape with respect to the first tubular body. During the connection between the proximal ends of the first signal lines and the terminal part, the second tubular body is advanced toward the first tubular body.

9 Claims, 16 Drawing Sheets

(51) Int. Cl.
*A61B 1/00* (2006.01)
*A61B 1/06* (2006.01)

(52) U.S. Cl.
CPC ...... *A61B 1/00097* (2022.02); *A61B 1/00133* (2013.01); *A61B 1/00135* (2013.01); *A61B 1/00137* (2013.01); *A61B 1/05* (2013.01); *A61B 1/051* (2013.01); *G02B 23/2407* (2013.01); *G02B 23/2469* (2013.01); *G02B 23/2484* (2013.01); *A61B 1/0676* (2013.01)

(58) Field of Classification Search
CPC ........... A61B 1/051; A61B 1/053; A61B 1/06; A61B 1/0676; A61B 1/07; A61B 1/00112; A61B 1/00114; A61B 1/00121; A61B 1/0011; A61B 1/00124; A61B 1/00089; A61B 1/00174; A61B 1/04; G02B 23/2407; G02B 23/2423; G02B 23/2476; G02B 23/2484; G02B 23/2492; G02B 23/2469
USPC ................. 600/109, 112, 110, 129, 160, 176
See application file for complete search history.

(56) References Cited

U.S. PATENT DOCUMENTS

| | | | | |
|---|---|---|---|---|
| 8,821,381 | B2* | 9/2014 | Akiba | A61B 1/00105 600/172 |
| 2004/0171912 | A1* | 9/2004 | Shimizu | A61B 1/042 600/112 |
| 2005/0228226 | A1* | 10/2005 | Muckner | A61B 1/0008 600/110 |
| 2007/0007360 | A1* | 1/2007 | Ogino | A61B 1/05 235/495 |
| 2009/0198106 | A1* | 8/2009 | Ichihashi | A61B 1/00048 600/178 |
| 2014/0288369 | A1* | 9/2014 | Henley | A61B 1/00096 600/109 |
| 2014/0303439 | A1* | 10/2014 | Scherr | A61B 1/05 600/112 |
| 2014/0336457 | A1* | 11/2014 | Kuhn | G02B 23/2423 600/109 |
| 2015/0094534 | A1 | 4/2015 | Yamada | |

FOREIGN PATENT DOCUMENTS

| | | |
|---|---|---|
| JP | H06-027393 | 2/1994 |
| JP | H09-192084 | 7/1997 |
| JP | H10-234649 | 9/1998 |
| JP | 2015-066287 | 4/2015 |

OTHER PUBLICATIONS

"Search Report of European Counterpart Application," dated Jun. 7, 2018, p. 1-p. 7.

"International Search Report (Form PCT/ISA/210) of PCT/JP2016/058008," dated May 31, 2016, with English translation thereof, pp. 1-5.

"Written Opinion of the International Searching Authority (Form PCT/ISA/237) of PCT/JP2016/058008," dated May 31, 2016, with English translation thereof, pp. 1-8.

* cited by examiner

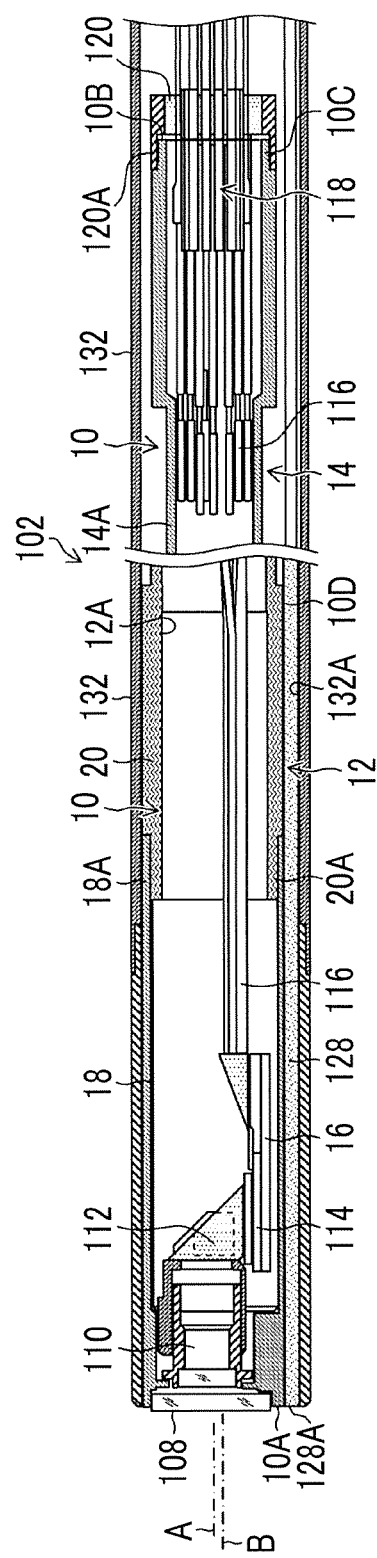

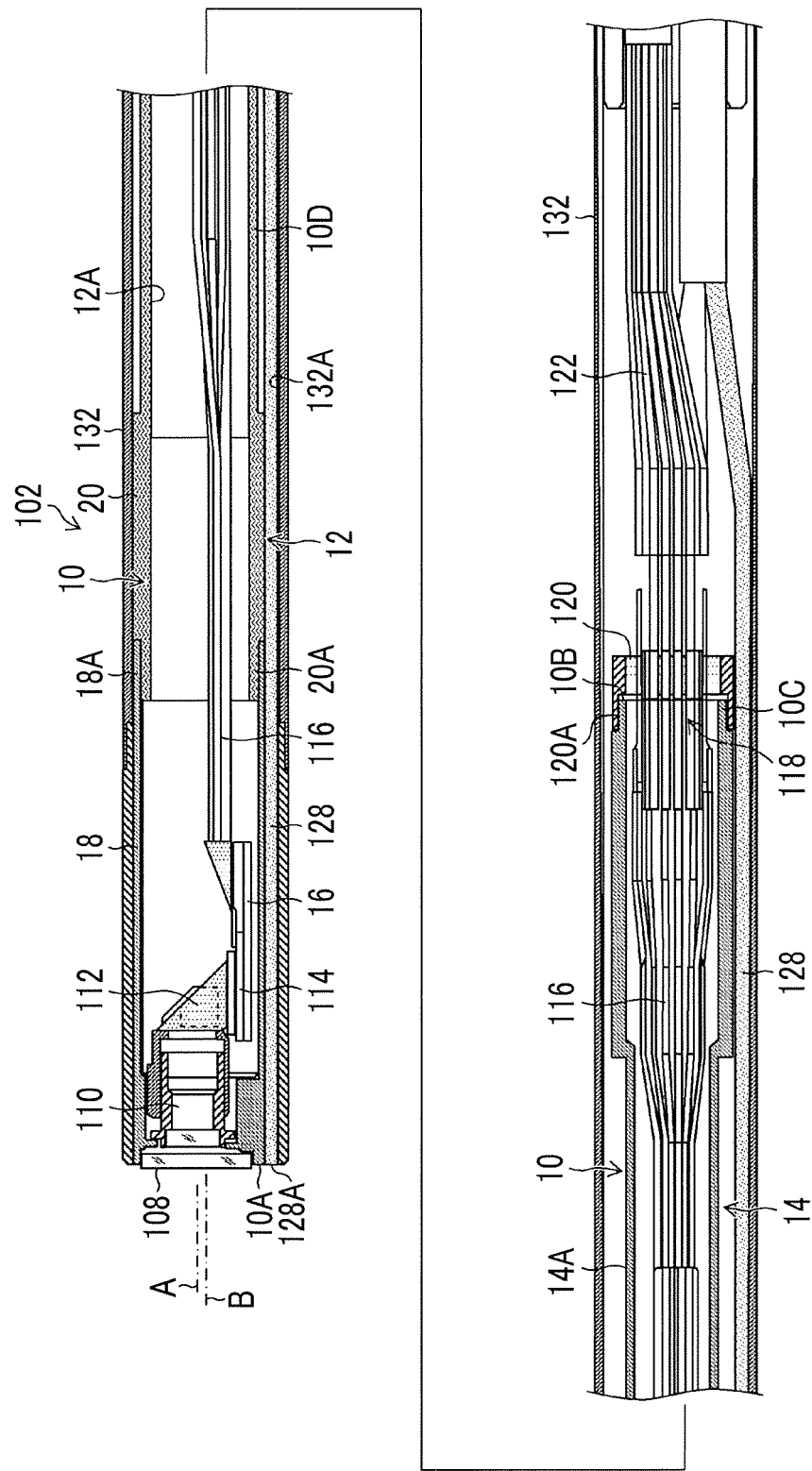

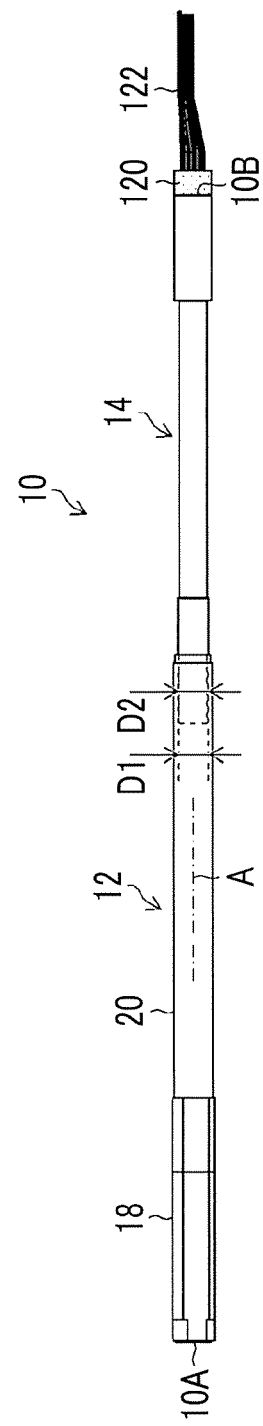

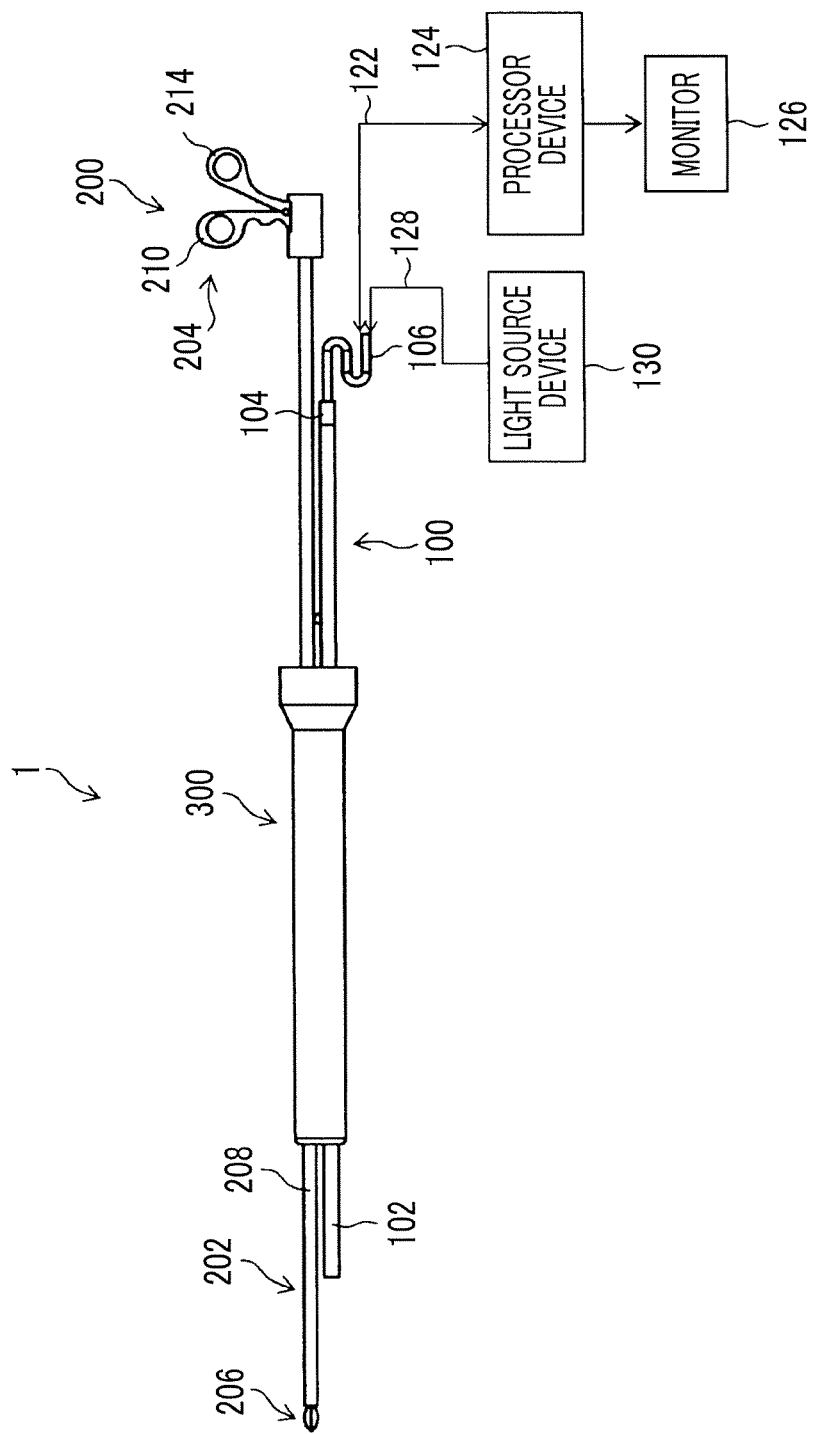

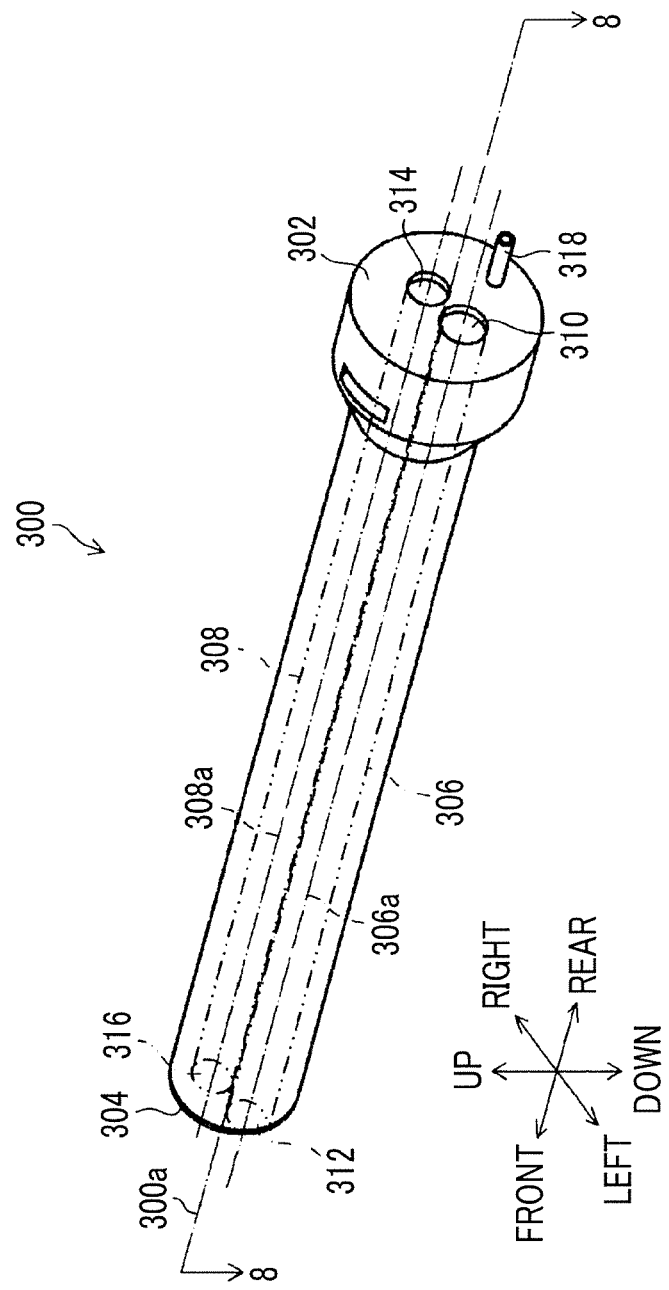

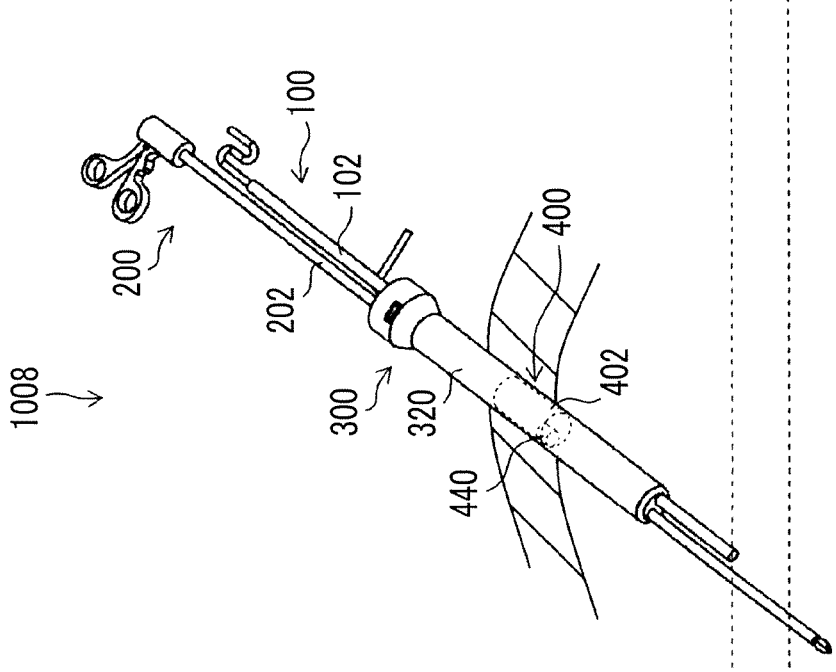
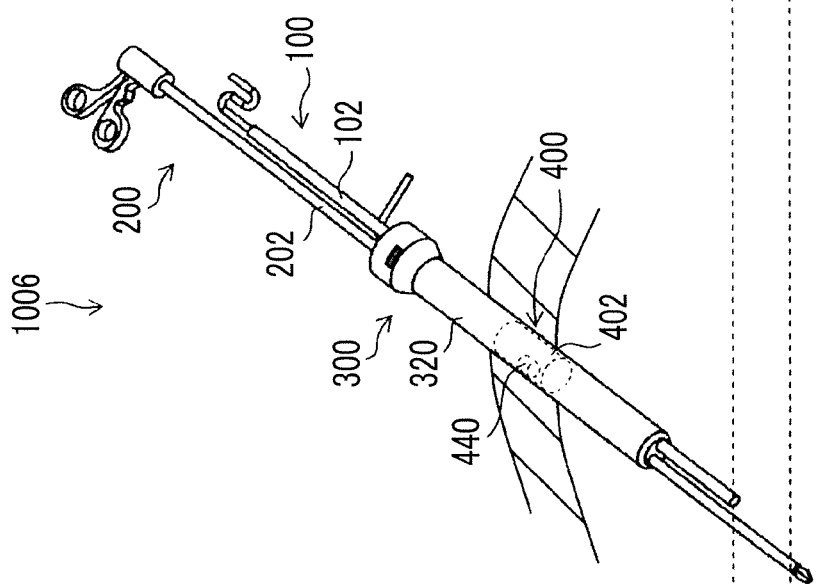

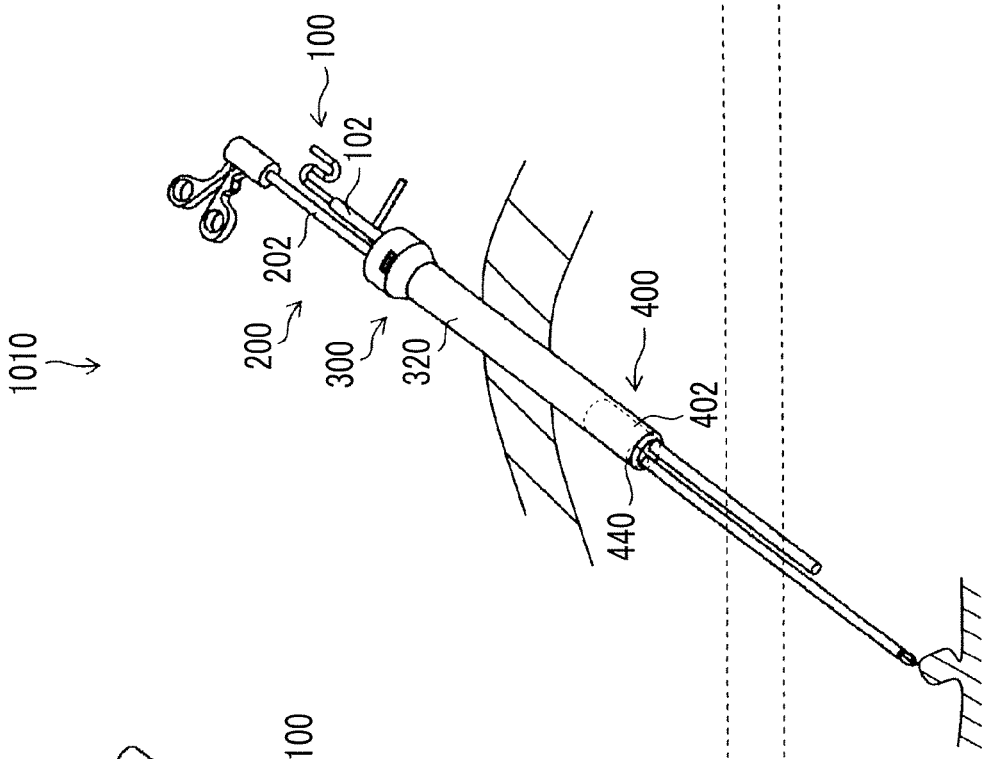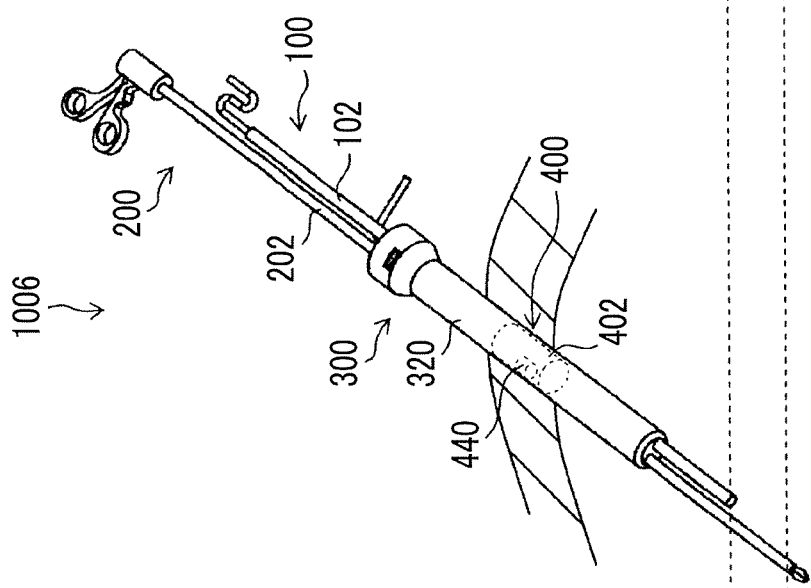

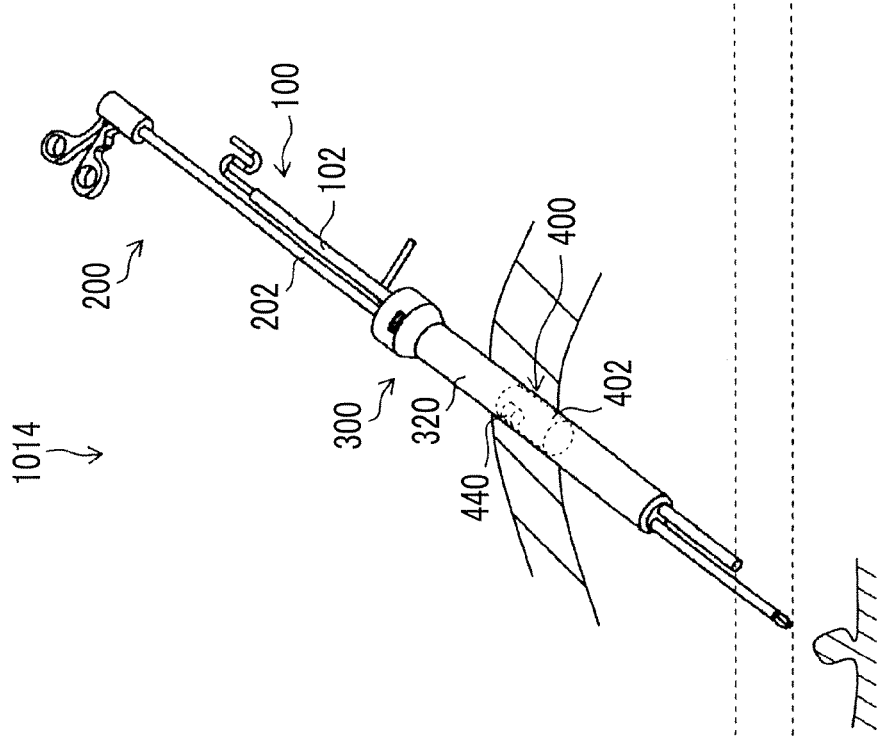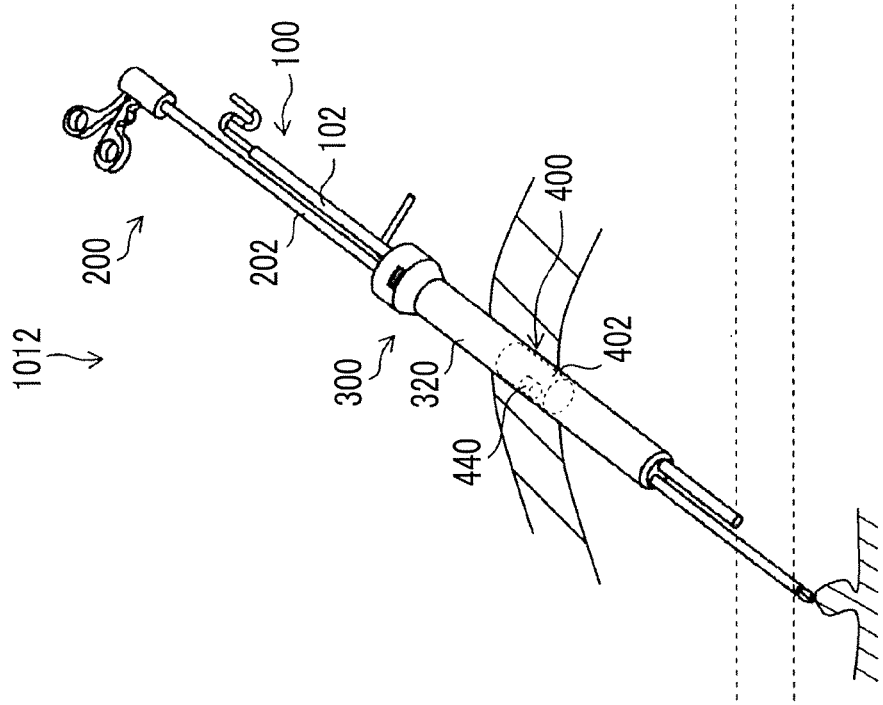

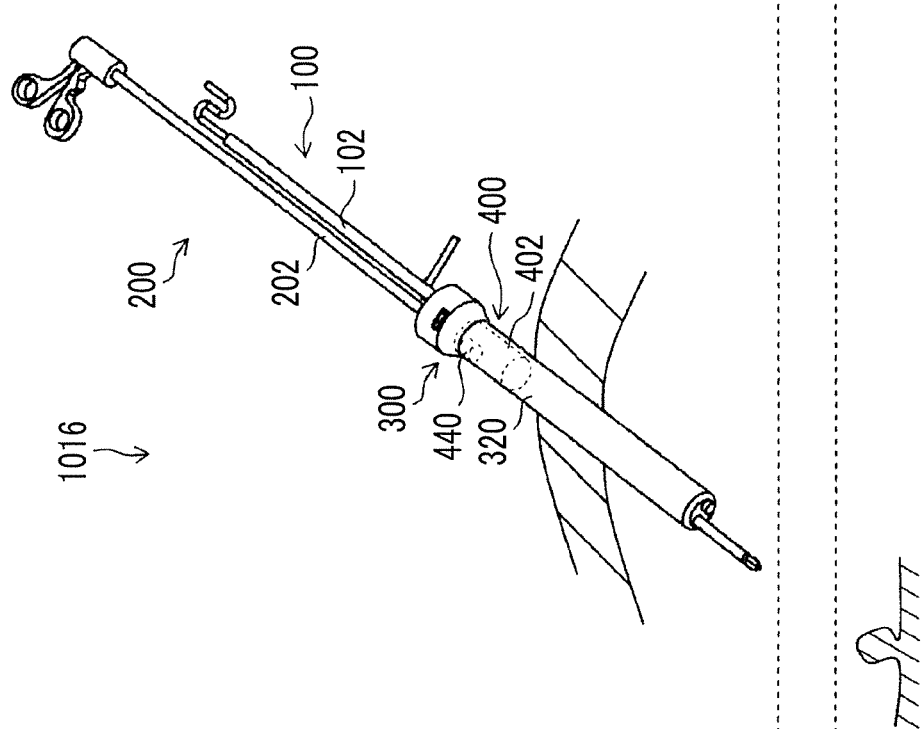
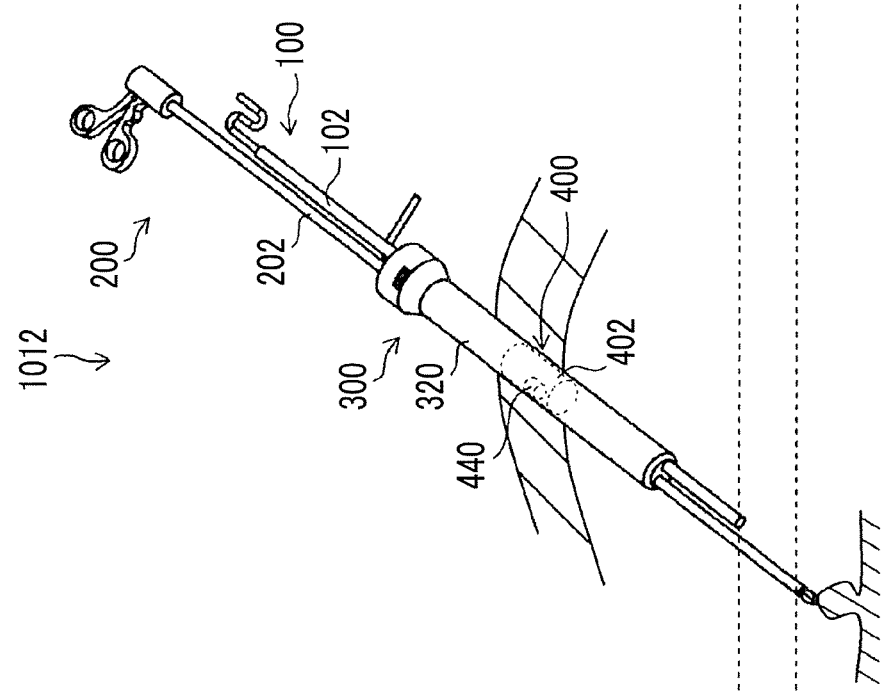

ENDOSCOPE

CROSS-REFERENCE TO RELATED APPLICATIONS

This application is a Continuation of PCT International Application No. PCT/JP2016/058008 filed on Mar. 14, 2016, which claims priority under 35 U.S.C. § 119(a) to Japanese Patent Application No. 2015-071819 filed on Mar. 31, 2015. Each of the above applications is hereby expressly incorporated by reference, in their entirety, into the present application.

BACKGROUND OF THE INVENTION

1. Field of the Invention

The present invention relates to an endoscope, and particularly, to an endoscope including an airtight casing that airtightly holds an optical member and an imaging device that are disposed at a distal end of an insertion part of the endoscope.

2. Description of the Related Art

Among endoscopes, an optical member and an imaging device are provided at a distal end of an insertion part of an endoscope called a rigid endoscope, and a plurality of signal lines that transmit electrical signals of the imaging device are wired in a proximal operating part via the insertion part from the distal end of the insertion part.

In the endoscopes, if water, such as humidity, enters the inside of the insertion part even slightly, fogging occurs on an inner surface of the optical member, a color filter of the imaging device deteriorates, or a terminal part that connects distal ends of the signal lines and the imaging device together corrodes. Thus, there is a problem that an abnormality may occur in an image.

Particularly, during autoclave sterilization processing in which the endoscope is sterilized while being pressurizing and depressurized by a high-pressure steam sterilizer, there is a concern that steam may pass through a slight gap formed in the insertion part to enter the insertion part.

Thus, JP1998-234649A (JP-H10-234649A) discloses an endoscope including an optical member, an imaging device, and an inner tube that accommodates signal lines in an airtight state.

In the endoscope of JP1998-234649A, a metallic inner tube is inserted into the inside of an outer tube constituting the outer tube of the insertion part from the distal end of the insertion part to the inside of the proximal operating part, and the optical member, the imaging device, and the signal lines are accommodated in an airtight state inside the inner tube. Additionally, a distal end opening of the inner tube is airtightly sealed by fixing a cover glass to a distal end of the inner tube with solder. Moreover, a proximal end opening is airtightly sealed by joining a partition wall part to a proximal end of the inner tube located inside the proximal operating part.

The partition wall part includes the terminal part, which is a signal relay part, and a sealing member. The terminal part is inserted through the partition wall part, and is connected to proximal ends of the signal lines. The sealing member is filled with between the partition wall part and the terminal part. Accordingly, the inside of the inner tube is airtightly held.

That is, in the endoscope of JP1998-234649A, the optical member, the imaging device, and the signal lines are airtightly held by the inner tube that is inserted through the inside of the outer tube and that is the airtight casing.

SUMMARY OF THE INVENTION

Meanwhile, in a case where the proximal ends of the signal lines and the terminal part are connected together, in order to easily perform a connection task, it is necessary to extend the proximal ends of the signal lines from the proximal end of the inner tube to a proximal end side by a predetermined length to connect the proximal ends of the signal lines and the terminal part together. That is, in order to easily perform a connection task, it is necessary to secure an extra length, which is equivalent to such a length that the signal lines are extended, in advance.

In the endoscope disclosed in JP1998-234649A, the inner tube is provided with a space that can accommodate a portion equivalent to the extra length of the signal lines after being connected to the terminal part, that is, the inner tube has a large diameter. Thus, there is no problem.

However, in the case of a small-diameter inner tube in which a portion equivalent to the extra length of the signal lines cannot be accommodated, the extra length cannot be secured for the signal lines. Thus, it is difficult to connect the proximal ends of the signal lines and the terminal part together.

The invention has been made in view of such circumstances, and an object thereof is to provide an endoscope that includes an airtight casing which accommodates an imaging device and signal lines (first signal lines) in an airtight state therein and that can connect proximal ends of the first signal lines and a signal relay part together without securing an extra length for the first signal lines.

In order to achieve the object of the invention, one aspect of the invention provides an endoscope comprising an insertion part inserted into the body. The insertion part includes an outer tube that forms an outer peripheral wall of the insertion part, an optical member disposed at a distal end of the insertion part, an imaging device that picks up an observation image obtained through the optical member, a first signal line that has a distal end connected to the imaging device and transmits a signal output from the imaging device, a signal relay part connected to the proximal end of the first signal line, a second signal line that has a distal end connected to the signal relay part and transmits a signal relayed from the first signal line via the signal relay part, a partition wall part that holds the signal relay part, and an airtight casing that is disposed inside the outer tube, has a distal end, a proximal end, and a longitudinal axis, and has a tubular shape of which the inside is hollow, the distal end being airtightly sealed by the optical member, the proximal end being airtightly sealed by the partition wall part, and the imaging device and the first signal line being accommodated in an airtight state therein. The airtight casing includes a first tubular body having a first holding part that holds the optical member, and a second tubular body having a second holding part that holds the partition wall part. The second tubular body has a second wall surface that faces a first wall surface of the first tubular body, slides on the first tubular body so as to be movable backward and forward along the longitudinal axis during the assembly of the airtight casing, and is fixed to the first tubular body after the assembly of the airtight casing.

According to the one aspect of the invention, the airtight casing is disposed inside the outer tube of the insertion part, the imaging device and the first signal line are accommodated inside the airtight casing, an opening of the distal end of the airtight casing is airtightly sealed by the optical member, and an opening of the proximal end of the airtight casing is airtightly sealed by a partition wall part. Accordingly, the imaging device and the first signal line can be accommodated in an airtight state inside the airtight casing.

Additionally, the airtight casing is constituted of the first tubular body and the second tubular body, and the second tubular body is disposed in a nested shape with respect to the first tubular body. During the assembly of the airtight casing, that is, during the connection between the proximal end of the first signal line and the signal relay part held by the partition wall part, the second tubular body is advanced toward the first tubular body. That is, the airtight casing is retracted in the direction of the longitudinal axis. Accordingly, during the connection between the proximal end of the first signal line and the signal relay part, the proximal end of the second tubular body is evacuated to the first tubular body side with respect to the signal relay part. Therefore, since the proximal end of the second tubular body does not become an obstacle during a connection task, the proximal end of the first signal line and the signal relay part can be easily connected together without securing an extra length for the first signal line.

Thereafter, the second tubular body is moved for evacuation from the first tubular body. That is, the airtight casing is extended in the direction of the longitudinal axis, and the partition wall part is held by the second holding part of the second tubular body. Accordingly, the airtight casing is assembled. Then, the second tubular body is fixed to the first tubular body after the assembly of the airtight casing.

As described above, according to the endoscope of the invention, the airtight casing that accommodates the imaging device and the first signal line in an airtight state therein is provided, and the proximal end of the first signal line and the signal relay part can be joined together without securing an extra length for the first signal line. Accordingly, according to the endoscope of the invention, the diameter of the airtight casing can be reduced. Thus, the diameter of the insertion part of the endoscope can be reduced.

In the one aspect of the invention, it is preferable that the first wall surface is an inner wall surface of the first tubular body, the second wall surface is an outer wall surface of the second tubular body, and the second tubular body is disposed inside the first tubular body.

According to the one aspect of the invention, the second tubular body is disposed in a nested shape with respect to the first tubular body by the second wall surface of the second tubular body facing the first wall surface of the first tubular body and the first wall surface and the second wall surface sliding on each other.

In the one aspect of the invention, it is preferable that the partition wall part has a fitted part on a distal end side thereof, and the second holding part has a fitting part that is airtightly and detachably fitted to the fitted part during the assembly of the airtight casing and is fixed to the fitted part after the assembly of the airtight casing.

According to the one aspect of the invention, the fitting part of the second holding part the second tubular body is airtightly fitted to the fitted part of the partition wall part during the assembly of the airtight casing, and the fitting part is fixed to the fitted part after the assembly of the airtight casing. Accordingly, the airtightness at the proximal end of the airtight casing can be reliably secured.

In the one aspect of the invention, it is preferable that the first tubular body has a distal-end-side tubular body, and a proximal-end-side tubular body connected to a proximal end the distal-end-side tubular body, and the distal-end-side tubular body has a fixing part that fixes the imaging device to the inside thereof.

In the one aspect of the invention, in order to fix the imaging device to the first tubular body, it is preferable to perform a fixing task via openings on both sides of the distal end side and the proximal end side of the first tubular body. For this reason, since the fixing task becomes more difficult as the axial length of the first tubular body becomes longer, the first tubular body is split into the distal-end-side tubular body and the proximal-end-side tubular body, and the imaging device is fixed to the fixing part of the distal-end-side tubular body of which the axial length becomes short. Accordingly, the fixing task of the imaging device becomes easy.

In one aspect of the invention, it is preferable that the second wall surface comes into close contact with the first wall surface without a gap.

According to the aspect of the invention, the airtightness in a sliding part between the second tubular body and the first tubular body can be reliably secured.

In the one aspect of the invention, it is preferable that the insertion part has an optical transmission member disposed between an inner wall surface of the outer tube and an outer wall surface of the airtight casing, and the optical transmission member has a light emission end surface exposed to a distal end surface of the insertion part.

According to the one aspect of the invention, the optical transmission member is not disposed inside the airtight casing, and the optical transmission member is disposed in a gap between the inner wall surface of the outer tube and the outer wall surface of the airtight casing. That is, since an increase in the diameter of the airtight casing resulting from the arrangement of the optical transmission member inside the airtight casing can be prevented, a concern of a decrease in airtightness accuracy resulting from an increase in the diameter of the airtight casing can be eliminated. In addition, it is preferable that the aperture angle of illumination light irradiated from the light emission end surface is 100 degrees or more. Accordingly, it is possible to cope with an angle of view that is wide although the diameter is small.

According to the endoscope of the invention, the airtight casing that accommodates the imaging device and the first signal line in an airtight state therein is provided, and the proximal end of the first signal line and the signal relay part can be connected together without securing an extra length for the first signal line.

BRIEF DESCRIPTION OF THE DRAWINGS

FIG. 3 is a cross-sectional view of main parts including a partial fracture of the insertion part of the endoscope.

FIG. 4 is a cross-sectional view of main parts of the endoscope illustrating a wiring form of optical fiber element wires inside the insertion part.

FIG. 5A is an assembly completion view of an airtight casing.

FIG. 6 is a schematic configuration view of an endoscopic surgical device related to the invention.

FIG. 7 is an external perspective view illustrating an overtube from the rear upper left direction.

FIGS. 11A and 11B are views illustrating a state when the treatment tool insertion part is pushed into the affected area side within the body cavity from the near side, FIG. 11A illustrates a state before the treatment tool insertion part is pushed, and FIG. 11B illustrates a state after the treatment tool insertion part is pushed.

FIGS. 12A and 12B are views illustrating a state when a treatment tool insertion part is pushed into an affected area side within a body cavity from the near side, FIG. 12A illustrates a state before the treatment tool insertion part is pushed in, and FIG. 12B illustrates a state after the treatment tool insertion part is pushed in.

FIGS. 13A and 13B are views illustrating a state when the treatment tool insertion part is pulled from the affected area side within a body cavity to the near side, FIG. 13A illustrates a state before the treatment tool insertion part is pulled, and FIG. 13B illustrates a state after the treatment tool insertion part is pulled.

FIGS. 14A and 14B are views illustrating a state when the treatment tool insertion part is pulled from the affected area side within a body cavity to the near side, FIG. 14A illustrates a state before the treatment tool insertion part is pulled, and FIG. 14B illustrates a state after the treatment tool insertion part is pulled.

DESCRIPTION OF THE PREFERRED EMBODIMENTS

Hereinafter, preferable embodiments of an endoscope related to the invention will be described according to the accompanying drawings.

[Endoscope 100]

Figure 1:
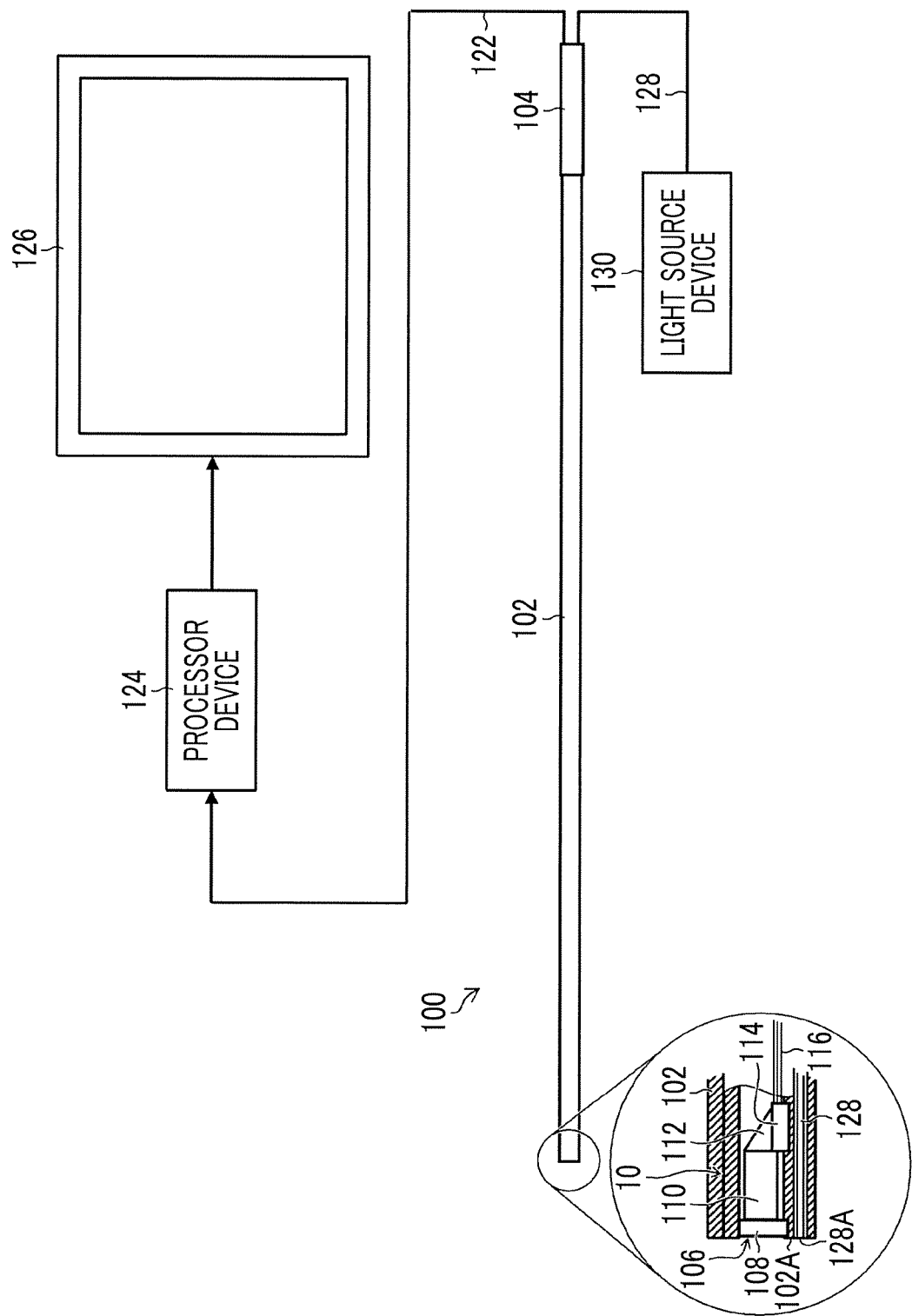
FIG. 1 is a configuration view of an endoscope of an embodiment.

FIG. 1 is a configuration view of an endoscope 100 of an embodiment, and illustrates a direct viewing type hard endoscope, such as a laparoscope, as the endoscope 100.

Figure 2:
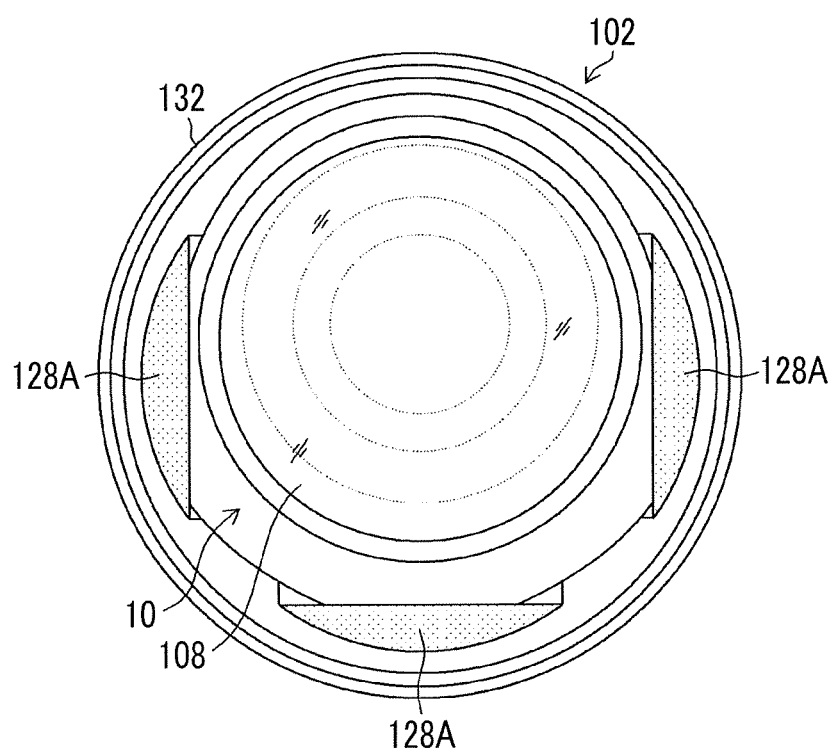
FIG. 2 is a front view of a distal end surface of an insertion part of the endoscope.

The endoscope 100 includes a cylindrical insertion part 102 inserted into a patient's body, and a cylindrical operating part 104 connected to a proximal end of the insertion part 102. FIG. 2 is a front view of a distal end surface 102A of the insertion part 102.

As illustrated in FIGS. 1 and 2, a cover glass 108, which constitutes a distal end of an optical member 106, is disposed on the distal end surface 102A of the insertion part 102. Additionally, as illustrated in an enlarged cross-sectional view of some main parts of FIG. 1, an imaging lens group 110, which constitutes a main body of the optical member 106, and a prism 112 are built inside the insertion part 102. Additionally, an imaging device 114, which picks up an observation image obtained through the optical member 106, and a plurality of first signal lines 116, which have their distal ends connected to the imaging device 114 and transmit image signals output from the imaging device 114, are built inside the insertion part 102.

Proximal ends of the first signal lines 116 are connected to a distal end of a terminal part 118 (refer to FIGS. 3 and 4) that is a signal relay part. The terminal part 118 is disposed to pass through a partition wall part 120 to be described below and is held in an airtight state at the partition wall part 120. Additionally, a distal end of a second signal line 122 is connected to a proximal end of the terminal part 118, the second signal line 122 extends from the operating part 104 to the outside as illustrated in FIG. 1, and a proximal end of the signal line 122 is connected to a processor device 124.

As the imaging device 114, a charge coupled device (CCD) type image sensor or a complementary metal oxide semiconductor (CMOS) image sensor can be used. In addition, an airtight casing 10 (refer to FIG. 5A and FIG. 5B) for airtightly holding the imaging lens group 110, a prism 112, the imaging device 114, and the first signal lines 116 will be described below.

The processor device 124 of FIG. 1 receives the image signals output via the first signal lines 116 and the second signal line 122 from the imaging device 114 to generate video signals, and outputs the video signals to a monitor 126. Accordingly, an image on the inside of the body is displayed on the monitor 126.

Additionally, a plurality of optical fiber element wires 128, which are optical transmission members, are built in the insertion part 102.

Proximal ends of the optical fiber element wires 128 extend from operating part 104 to the outside and are connected to a light source device 130. Accordingly, the light from the light source device 130 is supplied to the optical fiber element wires 128 and is irradiated from light emission end surfaces 128A of the optical fiber element wires 128, which are exposed to the distal end surface 102A of the insertion part 102, to the outside. The optical fiber element wires 128 will also be described below.

In the surgery using the endoscope 100, an affected area is irradiated with light of an opening angle of 100 degrees or more from the light emission end surfaces 128A of the optical fiber element wires 128. The irradiated affected area is imaged by the imaging device 114 via the optical member 106, and an operator operates a treatment tool (not illustrated) to perform treatment of the affected area while confirming the video through the monitor 126.

[Airtight Casing 10 of Endoscope 100]

FIG. 3 is a cross-sectional view of main parts including a partial fracture of the insertion part 102 of the endoscope 100, and illustrates a cross-section of the airtight casing 10 built in the insertion part 102. Although FIG. 4 is also the same cross-sectional view, particularly, a wiring form of the optical fiber element wires 128 inside the insertion part 102 is illustrated. Additionally, FIGS. 5A and 5B are configuration views of the airtight casing 10, FIG. 5A is an assembly completion view of the airtight casing 10, and FIG. 5B is a view illustrating a form before the assembly of the airtight casing 10 and illustrating a form when connecting the proximal ends of the first signal lines 116 and the terminal part 118 together.

As illustrated in FIGS. 3 and 4, the airtight casing 10 is disposed to be inserted through inside an outer tube 132 that forms an outer peripheral wall of the insertion part 102, and the length thereof in a longitudinal axis direction is made to be shorter than that the outer tube 132. Additionally, the airtight casing 10 is disposed such that a longitudinal axis A thereof is parallel to a longitudinal axis B of the outer tube 132, and is disposed at a position that is eccentric from the longitudinal axis B.

As illustrated in FIG. 5A, the airtight casing 10 has a distal end 10A, a proximal end 10B, and the longitudinal axis A.

Figure 5B:
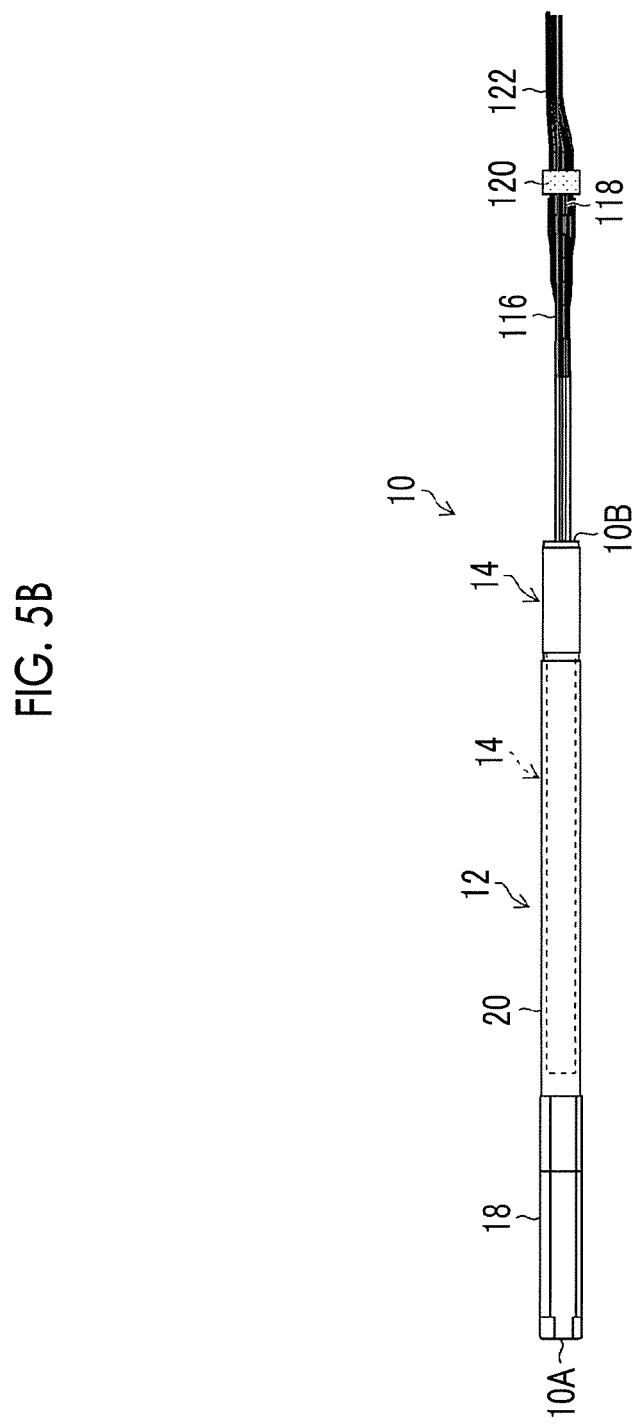
FIG. 5B is a view illustrating a form before the assembly of the airtight casing.

Additionally, the airtight casing 10 has a tubular shape of which the inside is hollow, an opening of the distal end 10A is airtightly sealed by the disk-like cover glass 108 of FIG. 1, and an opening of the proximal end 10B of FIG. 5B is airtightly sealed by the disk-like partition wall part 120. Accordingly, the imaging lens group 110, the prism 112, the imaging device 114, and the first signal lines 116 are accommodated in an airtight state inside the airtight casing 10.

As a sealing form of the cover glass 108 with respect the distal end 10A, a sealing form in which metal is coated in advance on a side surface of the cover glass 108 and the side surface and an inner peripheral surface of the distal end 10A that is a first holding part are anchored with solder can be exemplified. Additionally, as a sealing form of the partition wall part 120 with respect to the proximal end 10B, as illustrated in FIGS. 3 and 4, a sealing form in which a fitted part 120A provided on a distal end side of the partition wall part 120 and a fitting part 10C of the proximal end 10B that is a second holding part are bonded together with an adhesive or welding can be exemplified.

<First Tubular Body 12, Second Tubular Body 14>

As illustrated in FIGS. 5A and 5B, the airtight casing 10 consists of a first tubular body 12 disposed on a distal end side thereof and a second tubular body 14 disposed on a proximal end side thereof.

An internal diameter D1 on the proximal end side of the first tubular body 12 is made to be larger than an external diameter D2 on the distal end side of the second tubular body 14. As illustrated in FIGS. 3 and 4, an outer wall surface 14A that is a second wall surface of the second tubular body 14 is brought into sliding contact with an inner wall surface 12A that is a first wall surface of the first tubular body 12 in an airtightness held state. That is, the outer wall surface 14A faces the inner wall surface 12A, and the outer wall surface 14A is brought into close contact with the inner wall surface 12A without a gap.

Additionally, the first tubular body 12 and the second tubular body 14 are slidably attached so as to be movable relative to each other backward and forward along the longitudinal axis A. Accordingly, as illustrated in FIG. 5B, the airtight casing 10 before assembly is constituted as a double-tube structure consisting of the first tubular body 12 and the second tubular body 14, and is constituted as a telescopic structure that is extendable and retractable in the direction of the longitudinal axis A.

Additionally, during the assembly of the airtight casing 10, as illustrated in FIGS. 5A and 5B, the second tubular body 14 slides to be movable backward and forward movement along the longitudinal axis A with respect to the first tubular body 12. Additionally, the second tubular body 14 is fixed to the first tubular body 12 after the assembly of the airtight casing 10. This fixing form, that is, a fixing form between the proximal end of the first tubular body 12 and the distal end of the second tubular body 14 may be soldering or welding.

In addition, the internal diameter on the proximal end side of the first tubular body 12 is made to be smaller than the external diameter on the distal end side of the second tubular body 14, and an inner peripheral surface of the second tubular body 14 may be made to slide on an outer peripheral surface of the first tubular body 12 to form a nested shape.

The cover glass 108 is held by a distal end of the first tubular body 12, which is the distal end 10A of the airtight casing 10, as illustrated in FIGS. 3 and 4. The partition wall part 120 is held by a proximal end of the second tubular body, which is the proximal end 10B of the airtight casing 10.

Inside the first tubular body 12, the imaging lens group 110 and a prism 112 are disposed in close proximity to the a cover glass 108, and the imaging device 114 is fixed to the inner wall surface 12A of the first tubular body 12 via a fixing part 16.

The first signal lines 116 of which the proximal ends are connected to the imaging device 114 are inserted through the inside of the second tubular body 14 from the first tubular body 12, and the proximal ends thereof are connected to the distal end of the terminal part 118 by laser welding or the like. The terminal part 118 is disposed through the partition wall part 120 in an airtight state, and a distal end of the second signal line 122 is connected to the proximal end of the terminal part 118 by laser welding or the like.

In an extended form as illustrated in FIG. 5A, as illustrated in FIGS. 3 and 4, the fitting part 10C that is the second holding part of the airtight casing 10 is detachably and airtightly fitted to the fitted part 120A of the partition wall part 120.

<<Distal-End-Side Tubular Body 18 and Proximal-End-Side Tubular Body 20>>

As illustrated in FIG. 3 to FIG. 5B, the first tubular body 12 is constituted of a distal-end-side tubular body 18 disposed on a distal end side thereof and a proximal-end-side tubular body 20 disposed on a proximal end side thereof. A proximal end of the distal-end-side tubular body 18 and a distal end of the proximal-end-side tubular body 20 are connected together by fitting and are fixed together by laser welding or the like.

The cover glass 108, the imaging lens group 110, the prism 112, and the imaging device 114 are fixed to the distal-end-side tubular body 18.

During the task of fixing the cover glass 108, the imaging lens group 110, the prism 112, and the imaging device 114 to the first tubular body 12, the distal-end-side tubular body 18 and the proximal-end-side tubular body 20 are separated from each other, and the cover glass 108, the imaging lens group 110, the prism 112, and the imaging device 114 are fixed to the separated distal-end-side tubular body 18. Distal ends of the first signal lines 116 are connected to the imaging device 114 in advance. Thereafter, the proximal ends of the first signal lines 116 are inserted through the proximal-end-side tubular body 20 from the distal end thereof toward the proximal end thereof, and a proximal end 18A of the distal-end-side tubular body 18 and a distal end 20A of the proximal-end-side tubular body 20 are connected together by fitting. The proximal end 18A and the distal end 20A are fixed together by laser welding or the like as earlier described. Accordingly, the first tubular body 12 is configured.

[Arrangement Structure of Optical Fiber Element Wire 128]

As illustrated in FIGS. 3 and 4, the insertion part 102 has the optical fiber element wires 128 disposed in a gap between an inner wall surface 132A of the outer tube 132 and an outer wall surface 10D of the airtight casing 10. As illustrated in FIG. 1, each optical fiber element wire 128 has a light emission end surface 128A exposed to a distal end surface 102A of the insertion part 102.

As illustrated in FIG. 2, three optical fiber element wires 128 are disposed along the periphery of the cover glass 108. The three optical fiber element wires 128 are disposed in the gap between the outer tube 132 and the airtight casing 10, which is broadly formed by disposing the airtight casing 10 eccentrically from the outer tube 132.

[Feature of Endoscope 100 of Embodiment]

<First Feature>

According to the endoscope 100 of the embodiment, the airtight casing 10 is disposed inside the outer tube 132 of the insertion part 102, the imaging device 114 and the first signal lines 116 are accommodated inside the airtight casing 10, the opening of the distal end 10A of the airtight casing 10 is airtightly sealed by the cover glass 108, and the opening of the proximal end 10B of the airtight casing 10 is airtightly sealed by the partition wall part 120.

Accordingly, the imaging device 114 and the first signal lines 116 can be accommodated in an airtight state inside the airtight casing 10.

Additionally, the airtight casing 10 is constituted of the first tubular body 12 and the second tubular body 14, and the second tubular body 14 is disposed in a nested shape with respect to the first tubular body 12 as in a suitable second feature to be described below. During the assembly of the airtight casing 10, that is, during the connection between the proximal ends of the first signal lines 116 and the terminal part 118 held by the partition wall part 120, as illustrated in FIG. 5B, the second tubular body 14 is advanced toward the first tubular body 12. That is, the airtight casing 10 is retracted in the direction of the longitudinal axis A.

Accordingly, during the connection between the proximal ends of the first signal lines 116 and the terminal part 118, the fitting part 10C of the second tubular body 14 is evacuated to the first tubular body 12 side with respect to the terminal part 118. Therefore, since the fitting part 10C does not become an obstacle during a connection task, the proximal ends of the first signal lines 116 and the terminal part 118 can be easily connected together without securing an extra length for the first signal lines 116.

Thereafter, as illustrated in FIG. 5A, the second tubular body 14 is moved for evacuation from the first tubular body 12. That is, the airtight casing 10 is extended in the direction of the longitudinal axis A, and the fitting part 10C of the second tubular body 14 is fitted to the fitted part 120A of the partition wall part 120. Accordingly, the airtight casing 10 is assembled. After the assembly of the airtight casing 10, the distal end of the second tubular body 14 and the proximal end of the first tubular body 12 are fixed together by laser welding or the like.

As described above, according to the endoscope 100 of the embodiment, the airtight casing 10 that accommodates the imaging device 114 and the first signal lines 116 in an airtight state therein is provided, and the proximal ends of the first signal lines 116 and the terminal part 118 can be joined together without securing an extra length for the first signal lines 116. Accordingly, according to the endoscope 100 of the embodiment, the diameter of the airtight casing 10 can be reduced. Thus, the diameter of the insertion part 102 can be reduced.

<Second Feature>

The first wall surface is the inner wall surface 12A of the first tubular body 12, the second wall surface is the outer wall surface 14A of the second tubular body 14, and the second tubular body 14 is disposed in a nested shape inside the first tubular body 12.

That is, the outer wall surface 14A of the second tubular body 14 slides on the inner wall surface 12A of the first tubular body 12 in an airtightness held state.

Accordingly, the second tubular body 14 is disposed in a nested shape with respect to the first tubular body 12 by the outer wall surface 14A of the second tubular body 14 facing the inner wall surface 12A of the first tubular body 12 and the inner wall surface 12A and the outer wall surface 14A sliding on each other.

<Third Feature>

The partition wall part 120 has the fitted part 120A on the distal end side thereof, the proximal end 10B that is the second holding part has the fitting part 10C that is airtightly and detachably fitted to the fitted part 120A during the assembly of the airtight casing 10 and that is fixed to the fitted part 120A after the assembly of the airtight casing 10.

Accordingly, the fitting part 10C of the second tubular body 14 is airtightly fitted to the fitted part 120A of the partition wall part 120 during the assembly of the airtight casing 10, and the fitting part 10C is fixed to the fitted part 120A by laser welding or the like after the assembly of the airtight casing 10. Accordingly, the airtightness at the proximal end 10B of the airtight casing 10 can be reliably secured.

<Fourth Feature>

As illustrated in FIG. 3, the first tubular body 12 has the distal-end-side tubular body 18, and the proximal-end-side tubular body 20 connected to the proximal end the distal-end-side tubular body 18, and the distal-end-side tubular body 18 has the fixing part 16 that fixes the imaging device 114 to the inside thereof.

In order to fix the imaging device 114 to the first tubular body 12, it is preferable to perform a fixing task from opening parts on both sides of the distal end side and the proximal end side of the first tubular body 12. For this reason, since the fixing task becomes more difficult as the axial length of the first tubular body 12 becomes longer, the first tubular body 12 is split into the distal-end-side tubular body 18 and the proximal-end-side tubular body 20, and the imaging device 114 is fixed to the fixing part 16 of the distal-end-side tubular body 18 of which the axial length becomes short. Accordingly, the fixing task of the imaging device 114 becomes easy.

<Fifth Feature>

The outer wall surface 14A of the second tubular body 14 comes into close contact with the inner wall surface 12A of the first tubular body 12 without a gap.

Accordingly, the airtightness in a sliding part between the second tubular body 14 and the first tubular body 12 can be reliably secured.

<Sixth Feature>

The insertion part 102 has the optical fiber element wires 128 disposed in the gap between the inner wall surface 132A of the outer tube 132 and the outer wall surface 10D of the airtight casing 10, and each optical fiber element wire 128 has the light emission end surface 128A exposed to the distal end surface 102A of the insertion part 102.

That is, in the endoscope 100 of the embodiment, the optical transmission members are not disposed inside the airtight casing 10, and the optical fiber element wires 128 that are the optical transmission members are disposed between the inner wall surface 132A of the outer tube 132 and the outer wall surface 10D of the airtight casing 10.

Accordingly, since an increase in the diameter of the airtight casing 10 resulting from the arrangement of the optical transmission members inside the airtight casing 10 can be prevented, a concern of a decrease in airtightness resulting from an increase in the diameter of the airtight casing 10 can be eliminated.

In addition, it is preferable that the aperture angle of illumination light irradiated from the light emission end surface 128A is 100 degrees or more. Accordingly, it is possible to cope with an angle of view that is wide although the diameter is small.

Although the airtight casing 10 of the endoscope 100 related to the embodiments have been described above in detail, it is natural that the invention is not limited to the above embodiments, and various improvements and modifications may be made without departing from the scope of the invention.

Additionally, in the embodiments, the hard endoscope has been exemplified and described as the endoscope 100. However, the endoscope is not limited to the hard endoscope, and the invention can also be applied to a flexible endoscope in which an insertion part of an endoscope has a flexible part, a curved part, and a distal end rigid part.

Usage Example of Endoscope 100

FIG. 6 is a schematic configuration view of the endoscope 100 applied to the endoscopic surgical device 1.

The endoscopic surgical device 1 includes an endoscope 100 that observes the inside of a patient's body cavity, a treatment tool 200 for examining or treating an affected area within the patient's body cavity, and an overtube 300 that guides the endoscope 100 and the treatment tool 200 into the body cavity.

As illustrated in FIG. 1, the treatment tool 200 consists of, for example, forceps, and includes an elongated treatment tool insertion part 202 that is inserted into a body cavity, an operating part 204 that is provided on the proximal end side of the treatment tool insertion part 202 and is gripped by an operator, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is coupled to the fixed handle 210 in a rotationally movable manner via a rotational movement pin. A proximal end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the rotational movement operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

FIG. 7 is an external perspective view illustrating the overtube 300 from the rear upper left direction.

The overtube 300 has an endoscope insertion passage 306 through which the insertion part 102 of the endoscope 100 is inserted so as to be movable backward and forward, and a treatment tool insertion passage 308 through which the treatment tool insertion part 202 of the treatment tool 200 is inserted so as to be movable backward and forward.

The endoscope insertion passage 306 has a diameter such that at least the insertion part 102 is insertable therethrough with an endoscope insertion axis 306a parallel to a reference axis 300a representing a central axis of the entire overtube 300 as a central axis, and has a space portion within the overtube 300, which passes through the overtube 300 from a proximal end surface 302 to a distal end surface 304. The endoscope insertion axis 306a is equivalent to the position of an axis of the insertion part 102 inserted through the endoscope insertion passage 306.

The proximal end surface 302 is provided with an endoscope insertion port 310 that allows the insertion part 102 to be inserted into the endoscope insertion passage 306 therethrough, and the distal end surface 304 is provided with an endoscope delivery port 312 that allows the insertion part 102 inserted into the endoscope insertion passage 306 to be delivered to the outside therethrough.

The treatment tool insertion passage 308 has a diameter such that at least the treatment tool insertion part 202 is insertable therethrough with a treatment tool insertion axis 308a parallel to the reference axis 300a as a central axis, and has a space portion within the overtube 300, which passes through the overtube 300 from the proximal end surface 302 to the distal end surface 304. The treatment tool insertion axis 308a is equivalent to the position of an axis of the treatment tool insertion part 202 inserted through the treatment tool insertion passage 308.

The proximal end surface 302 is provided with a treatment tool insertion port 314 that allows the treatment tool insertion part 202 to be inserted into the treatment tool insertion passage 308 therethrough, and the distal end surface 304 is provided with a treatment tool delivery port 316 that allows the treatment tool insertion part 202 inserted into the treatment tool insertion passage 308 to be delivered to the outside therethrough.

In addition, regarding the position and orientation of a space where the overtube 300 is disposed, terms called forward, backward, left, right, up, and down are used with the orientation from the proximal end surface 302 in a direction along the reference axis 300a to the distal end surface 304 defined as the forward and with the orientation from the reference axis 300a to the endoscope insertion axis 306a defined as the left.

Figure 8:
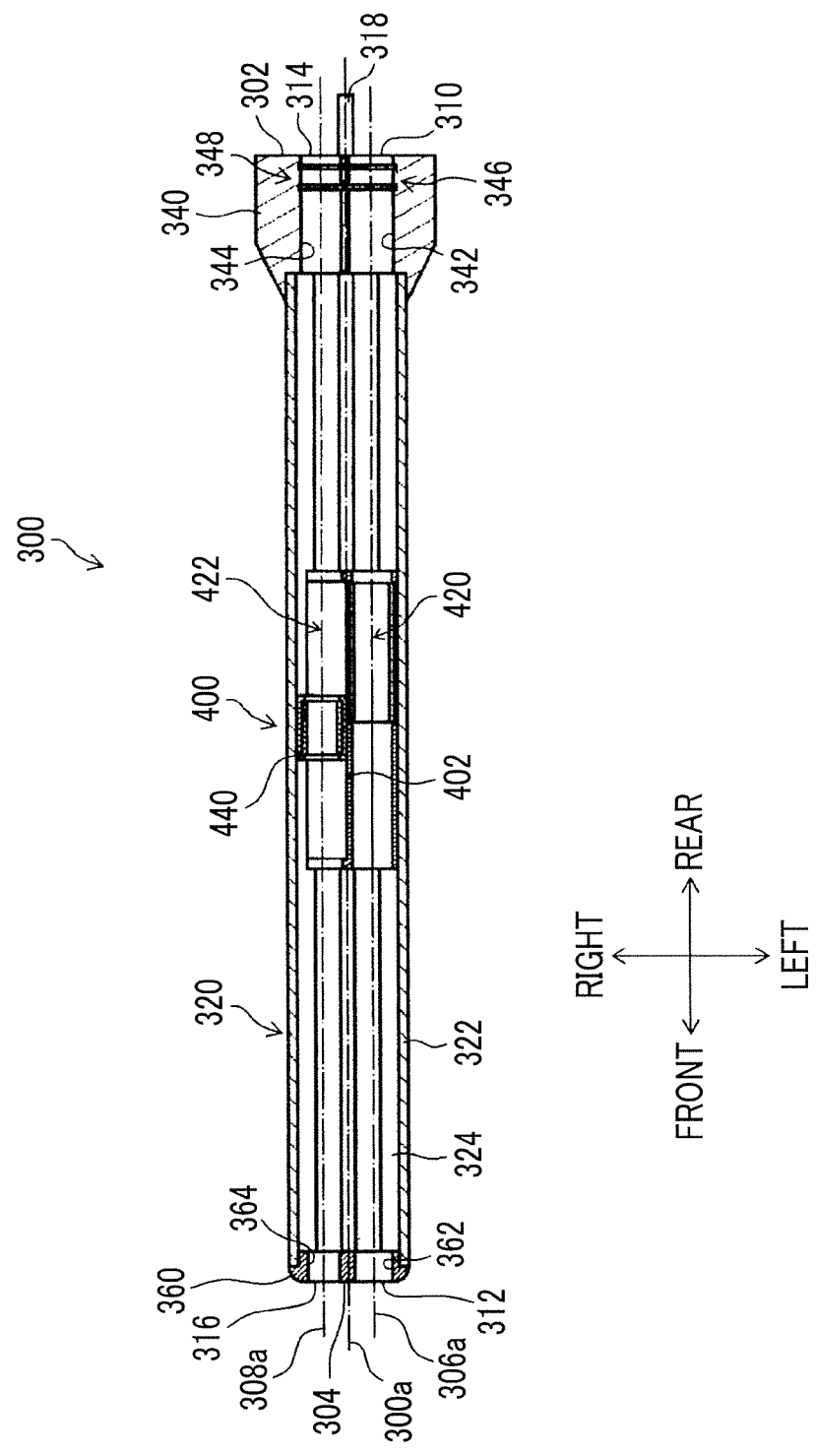
FIG. 8 is a cross-sectional view, taken along line 8-8 of FIG. 7, illustrating an internal structure of the overtube.

FIG. 8 is a cross-sectional view (a cross-sectional view taken along line 8-8 of FIG. 7) illustrating the internal structure of the overtube 300, and illustrates a cross-section cut in a plane that includes the reference axis 300a and is orthogonal to an upward-downward direction. In the present specification, a cross-sectional view simply refers to as a cross-sectional view taken along the same plane as that of FIG. 8.

The overtube 300 has an overtube body 320 that occupies the substantial entirety of the overtube in the forward-backward direction, a proximal end cap 340 disposed at a rear part of the overtube 300, a distal end cap 360 disposed at a distal end part of the overtube, and a slider 400 disposed inside the overtube 300.

The overtube body 320 is formed in an elongated cylindrical shape having the reference axis 300a as a central axis using hard resins, metals, or the like, and has an outer wall 322 that surrounds an outer periphery, and a lumen 324 that penetrates from a proximal end of the overtube body 320 to a distal end thereof.

The endoscope insertion axis 306a and the treatment tool insertion axis 308a pass into the lumen 324, and a space serving as the endoscope insertion passage 306 and the treatment tool insertion passage 308 is provided.

Additionally, the lumen 324 serves as an air supply pipe line through which a pneumoperitoneum gas sent thereinto from an air supply connector 318 passes.

The proximal end cap 340 is attached to a proximal end of the overtube body 320, and is formed in a columnar shape of which the diameter is made larger than the external diameter of the overtube body 320 using hard resins, metals, or the like. The proximal end cap 340 has a flat rear end surface serving as the proximal end surface 302 of an overtube 300 on a rear side thereof and has through-holes 342 and 344 that penetrates from the proximal end surface 302 to the lumen 324 of the overtube body 320.

The through-hole 342 has its central axis disposed coaxially with the endoscope insertion axis 306a, and forms a portion of the endoscope insertion passage 306. An opening of the through-hole 342 in the proximal end surface 302 is equivalent to the above-described endoscope insertion port 310.

The through-hole 344 has its central axis disposed coaxially with the treatment tool insertion axis 308a, and forms a portion of the treatment tool insertion passage 308. An opening of the through-hole 344 in the proximal end surface 302 is equivalent to the above-described treatment tool insertion port 314.

Valve members 346 and 348 are respectively disposed in the through-hole 342 and the through-hole 344. As the valve members 346 and 348, for example, there are provided slits that are open only in a case where the insertion part 102 and the treatment tool insertion part 202 are inserted therethrough and that are sealed up with outer peripheral surfaces of the insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 illustrated in FIG. 8 is attached to the distal end of the overtube body 320, and is formed of hard resins, metals, or the like. The distal end cap 360 has a front surface serving as the distal end surface 304 of the overtube 300 on a front side thereof and has through-holes 362 and 364 that penetrates from the lumen 324 of the overtube body 320 to the distal end surface 304.

The through-hole 362 has its central axis disposed coaxially with the endoscope insertion axis 306a, and forms a portion of the endoscope insertion passage 306. An opening of the through-hole 362 in the distal end surface 304 is equivalent to the above-described endoscope delivery port 312.

The through-hole 364 has its central axis disposed coaxially with the treatment tool insertion axis 308a, and forms a portion of the treatment tool insertion passage 308. An opening of the through-hole 364 in the distal end surface 304 is equivalent to the above-described treatment tool delivery port 316.

The slider 400 illustrated in FIG. 8 is accommodated within the lumen 324 of the overtube body 320, and is supported so as to be movable backward and forward in the direction of the reference axis 300a.

The slider 400 is coupled to the insertion part 102 of the endoscope 100 inserted through the endoscope insertion passage 306 and the treatment tool insertion part 202 inserted through the treatment tool insertion passage 308, and moves one backward and forward in an interlocking manner with the backward and forward movement of the other in the forward-backward direction.

Additionally, the slider 400 is provided with a range of play where the insertion part 102 does not interlock with the backward and forward movement of the treatment tool insertion part 202 in the axial direction. That is, the insertion part 102 interlocks with the backward and forward movement of the treatment tool insertion part 202 in the axial direction with play.

Accordingly, if an operator performs the backward and forward movement operation of the treatment tool insertion part 202 in the axial direction, the insertion part 102 also moves backward and forward in an interlocking manner. Thus, the visual field, orientation, and the like of the endoscope 100 can be changed as intended by the operator. Hence, an assistant (endoscopic technician) who operates the endoscope 100 apart from the operator becomes unnecessary, and a troublesome condition in which the operator should instruct an assistant about the visual field, orientation, and the like of the endoscope 100 serially can be eliminated.

Additionally, in a case where the displacement of the treatment tool insertion part 202 in the axial direction is small, the insertion part 102 does not interlock. Therefore, the size of a target to be observed within an observation image can be prevented from fluctuating unnecessarily, a sense of perspective can be suitably maintained, and a stable observation image can be provided.

Figure 9:
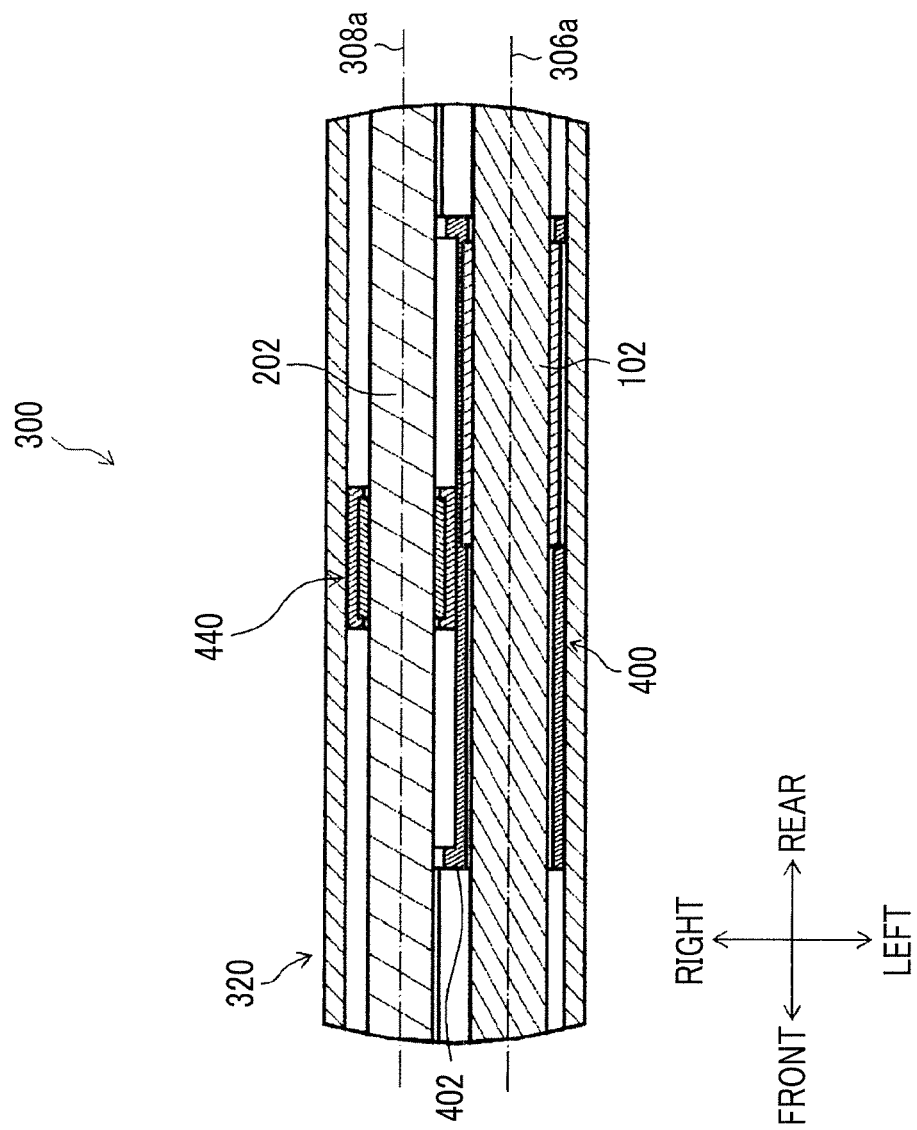
FIG. 9 is an enlarged cross-sectional view illustrating a portion of FIG. 8.

FIG. 9 is an enlarged cross-sectional view illustrating a portion, in which the slider 400 is disposed in FIG. 8, and illustrates a state where the insertion part 102 and the treatment tool insertion part 202 have been inserted through the endoscope insertion passage 306 and the treatment tool insertion passage 308, respectively.

As illustrated in FIG. 9, the slider 400 has a slider body 402. The slider body 402 is supported so as to be movable backward and forward in the forward-backward direction within the lumen 324, and is supported in a state where the movement of the slider body in the upward-downward direction and in the leftward-rightward direction and the rotation thereof in all directions is restricted.

Additionally, a range where the slider 400 moves backward and forward in the forward-backward direction with respect to the overtube body 320 becomes a range having a position where the slider 400 abuts against the proximal end cap 340 as a rear end, and having a position where the slider abuts against the distal end cap 360 as a front end.

An endoscope coupling part 420 is provided on the left side of the slider body 402, and secures a space serving as the endoscope insertion passage 306 within the lumen 324 of the overtube body 320. The slider 400 also moves backward and forward in an interlocking manner with the backward and forward movement of the insertion part 102 in the forward-backward direction.

In the overtube 300, the insertion part 102 and the treatment tool insertion part 202 are coupled together by the slider 400.

Next, an example of an operation method using the endoscopic surgical device 1 will be described.

FIGS. 10A to 14 are explanatory views illustrating states when the endoscopic surgical device 1 is operated.

Figure 10A:
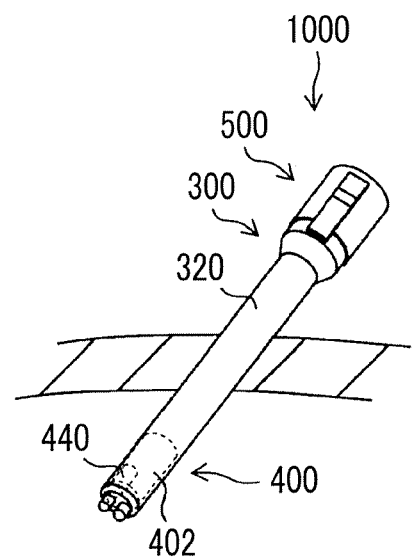
FIG. 10A is a view illustrating a state when the overtube is inserted into a body wall.
Figure 10B:
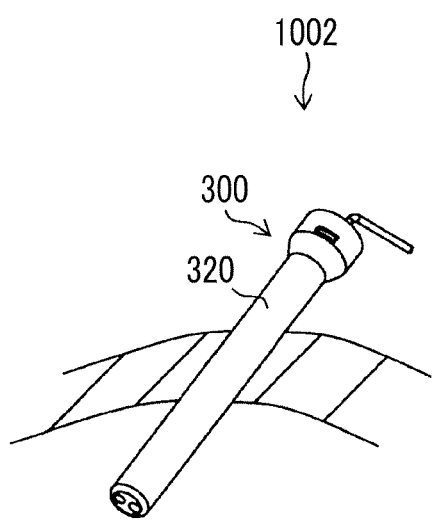
FIG. 10B is a view illustrating a state when the overtube is inserted into the body wall.
Figure 10C:
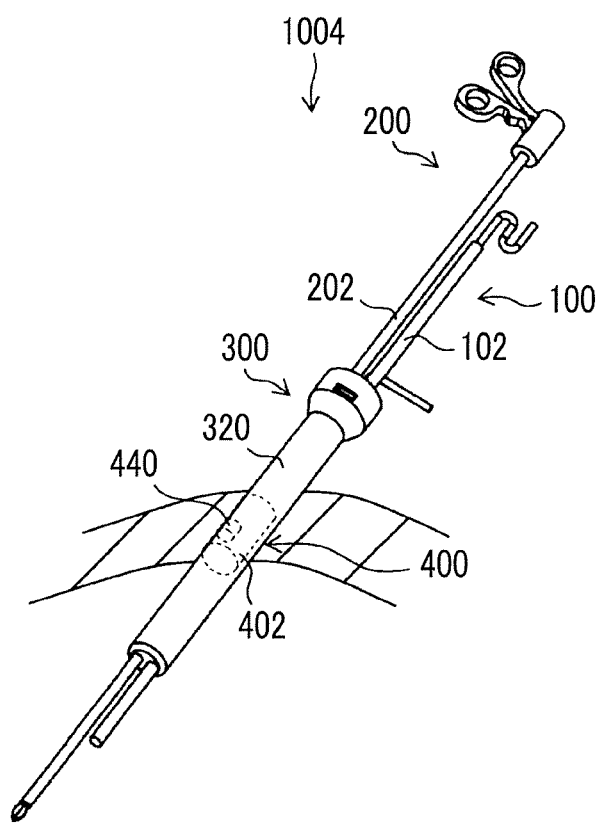
FIG. 10C is a view illustrating a state when the overtube is inserted into the body wall.

FIG. 10A to FIG. 10C are views illustrating states when the overtube 300 is inserted into a body wall.

FIGS. 11 and 12 are views illustrating states when the treatment tool insertion part 202 is pushed into an affected area side within a body cavity from the near side.

FIGS. 13 and 14 are views illustrating states when the treatment tool insertion part 202 is pulled from the affected area side within the body cavity to the near side.

First, as a preparation step for starting the operation of the endoscopic surgical device 1, the overtube 300 is inserted into a skin-incised area formed in a body wall in a state where the inner needle 500 is inserted through the endoscope insertion passage 306 and the treatment tool insertion passage 308 of the overtube 300, and the overtube 300 is inserted into a body cavity as in a state, indicated by reference sign 1000, of FIG. 10A.

Next, the inner needle 500 is extracted from the endoscope insertion passage 306 and the treatment tool insertion passage 308, as in a state, indicated by reference sign 1002, of FIG. 10B.

Next, the insertion part 102 is inserted into the endoscope insertion passage 306 from the endoscope insertion port 310 of the overtube 300, and the distal end of the insertion part 102 is delivered from the endoscope delivery port 312.

In this case, the insertion part 102 allows the endoscope coupling part 420 of the slider 400 to be inserted therethrough, and is coupled to the slider body 402 as described above. Accordingly, the insertion part 102 and the slider 400 are brought into an integrally moving state.

Subsequently, the treatment tool insertion part 202 is inserted into the treatment tool insertion passage 308 from the treatment tool insertion port 314 of the overtube 300, and the distal end of the treatment tool insertion part 202 is delivered from the treatment tool delivery port 316.

In this case, the treatment tool insertion part 202 allows a sleeve 440 of a treatment tool coupling part 422 of the slider 400 to be inserted therethrough, and is coupled to the sleeve 440 as described above. Accordingly, the treatment tool insertion part 202 and the sleeve 440 are brought into an integrally moving state.

If the preparation step is performed in this way, it will be in a state that can start operation of the endoscopic surgical device 1 as in a state, indicated by reference sign 1004, of FIG. 10C.

Next, a case where the treatment tool insertion part 202 is pushed into an affected area side within a body cavity from the near side will be described with reference to FIGS. 11 and 12.

First, in a case where the treatment tool insertion part 202 is minutely displaced in the axial direction as in a state, indicated by reference sign 1008, of the FIG. 11B from a state, indicated by reference sign 1006, of FIG. 11A, only the treatment tool insertion part 202 moves backward and forward, and the slider 400 does not move backward and forward. Hence, since the insertion part 102 does not move backward and forward, the range of an observation image displayed on the monitor 126 does not vary. For this reason, the size of an object to be observed can be prevented from fluctuating according to the minute displacement of the treatment tool insertion part 202, a sense of perspective can be suitably maintained, and a stable observation image can be obtained.

In contrast, in a case where the treatment tool insertion part 202 is greatly displaced in the axial direction like from a state, indicated by reference sign 1006, of FIG. 12A, which is the same state as reference sign 1010 of FIG. 11A, to a state, indicated by reference sign 1006, of FIG. 12B, and the slider 400 moves backward and forward in an interlocking manner with the backward and forward movement of the treatment tool insertion part 202. In this case, since the insertion part 102 moves backward and forward, the range of an observation image displayed on the monitor 126 is continuously changed so as to follow the backward and forward movement of the treatment tool insertion part 202. Accordingly, since the size of a target to be observed varies according to the operation of the treatment tool 200, it is possible for an operator to simply obtain a desired image.

Additionally, the same is true in a case where the treatment tool insertion part 202 is pulled from an affected area side within a body cavity to the near side.

That is, in a case where the treatment tool insertion part 202 is minutely displaced in the axial direction like from a state, indicated by reference sign 1012, of FIG. 13A to a state, indicated by reference sign 1014, of FIG. 13B, only the treatment tool insertion part 202 moves backward and forward, and the slider 400 does not move backward and forward. Hence, since the insertion part 102 does not move backward and forward, the range of an observation image displayed on the monitor 126 does not vary. For this reason, the size of an object to be observed can be prevented from fluctuating according to the minute displacement of the treatment tool insertion part 202, a sense of perspective can be suitably maintained, and a stable observation image can be obtained.

In contrast, in a case where the treatment tool insertion part 202 is greatly displaced in the axial direction like from a state, indicated by reference sign 1012, of FIG. 14A, which is the same state as reference sign 1012 of FIG. 13A, to a state, indicated by reference sign 1016, of FIG. 14B, the slider 400 moves backward and forward in an interlocking manner with the backward and forward movement of the treatment tool insertion part 202. In this case, since the insertion part 102 moves backward and forward, the range of an observation image displayed on the monitor 126 is continuously changed so as to follow the backward and forward movement of the treatment tool insertion part 202. Accordingly, since the size of a target to be observed varies according to the operation of the treatment tool 200, it is possible for an operator to simply obtain a desired image.

EXPLANATION OF REFERENCES

1: endoscopic surgical device
10: airtight casing
12: first tubular body
14: second tubular body
16: fixing part
18: distal-end-side tubular body
20: proximal-end-side tubular body
100: endoscope
102: insertion part
104: operating part
106: optical member
108: cover glass
110: imaging lens group
112: prism
114: imaging device
116: first signal line
118: terminal part
120: partition wall part
122: second signal line
124: processor device
126: monitor
128: optical fiber element wire
130: light source device
132: outer tube
200: treatment tool
202: treatment tool insertion part
204: operating part
206: treatment part
300: overtube
302: proximal end surface
304: distal end surface
306: endoscope insertion passage
308: treatment tool insertion passage
310: endoscope insertion port
312: endoscope delivery port 314: treatment tool insertion port
316: treatment tool delivery port
318: air supply connector
320: overtube body
322: outer wall
324: lumen
340: proximal end cap
342, 344: through-hole
346, 348: valve member
360: distal end cap
362, 364: through-hole
400: slider
402: slider body
420: endoscope coupling part
422: treatment tool coupling part
440: sleeve

What is claimed is:

1. An endoscope comprising
an insertion part inserted into a body,
wherein the insertion part includes
an outer tube that forms an outer peripheral wall of the insertion part,
an optical member disposed at a distal end of the insertion part,
an image sensor that picks up an observation image obtained through the optical member,
a first signal line that has a distal end connected to the image sensor and transmits a signal output from the image sensor,
a signal line connector connected to a proximal end of the first signal line,
a second signal line that has a distal end connected to the signal line connector and transmits a signal relayed from the first signal line via the signal line connector,
a partition wall part that holds the signal line connector, wherein the signal line connector is disposed to pass through the partition wall part, and
an airtight casing that is disposed inside the outer tube, has a distal end, a proximal end, and a longitudinal axis, and has a tubular shape of which the inside is hollow, the distal end being airtightly sealed by the optical member, the proximal end being airtightly sealed by the partition wall part, and the image sensor and the first signal line being accommodated in an airtight state therein,
wherein the airtight casing includes
a first tubular body, and
a second tubular body, disposed on a proximal end of the first tubular body, having a second holding part that holds the partition wall part,
wherein the first tubular body has a distal-end-side tubular body, holding the optical member and the image sensor, and a proximal-end-side tubular body, through which the first signal line connected to the image sensor is inserted, and a proximal end of the distal-end-side tubular body is connected to a distal end of the proximal-end-side tubular body,
wherein the second tubular body has a second wall surface that faces a first wall surface of the first tubular body, and an outer circumference of the second tubular body has a diameter which enables the second tubular body to slide inside the first tubular body along the longitudinal axis,
wherein the second tubular body is disposed in a nested shape inside the first tubular body, and the second wall surface of the second tubular body and the first wall surface of the first tubular body are slidable on each other in the airtight state of the airtight casing.

2. The endoscope according to claim 1,
wherein the first wall surface is an inner wall surface of the first tubular body,
wherein the second wall surface is an outer wall surface of the second tubular body, and
wherein the second tubular body is disposed inside the first tubular body.

3. The endoscope according to claim 1,
wherein the partition wall part has a fitted part on a distal end side thereof, and
wherein the second holding part has a fitting part that is airtightly and detachably fitted to the fitted part.

4. The endoscope according to claim 1,
wherein the distal-end-side tubular body has a fixing part that fixes the image sensor to the inside thereof.

5. The endoscope according to claim 1,
wherein the second wall surface comes into close contact with the first wall surface without a gap.

6. The endoscope according to claim 1,
wherein the insertion part has an optical fiber wire disposed between an inner wall surface of the outer tube and an outer wall surface of the airtight casing, and
wherein the optical fiber wire has a light emission end surface exposed to a distal end surface of the insertion part.

7. The endoscope according to claim 1,
wherein the image sensor is disposed inside the distal-end-side tubular body.

8. The endoscope according to claim 1,
wherein the airtight casing is a telescopic structure having the first tubular body and the second tubular body.

9. The endoscope according to claim 1,
wherein the proximal-end-side tubular body of the first tubular body and the second tubular body are formed in a straight tubular shape.

* * * * *